United States Patent [19]

Dyfvermark

[11] Patent Number: 4,975,057
[45] Date of Patent: Dec. 4, 1990

[54] DENTAL APPLIANCE

[76] Inventor: Ulf T. Dyfvermark, Kungsgatan 10, S-453 00 Lysekil, Sweden

[21] Appl. No.: 310,824

[22] Filed: Feb. 14, 1989

[30] Foreign Application Priority Data

Feb. 19, 1988 [SE] Sweden .............................. 8800570

[51] Int. Cl.⁵ ............................................ A61C 17/06
[52] U.S. Cl. ......................................... 433/93; 433/91
[58] Field of Search ........................... 433/93, 136, 139

[56] References Cited

U.S. PATENT DOCUMENTS

| 1,122,086 | 12/1914 | Dunlop .................................. 433/93 |
| 2,152,391 | 3/1939 | Spahn .................................. 433/136 |
| 2,637,107 | 5/1953 | Daigle .................................. 433/136 |
| 2,823,455 | 2/1958 | Sprague .................................. 433/93 |
| 3,090,122 | 5/1963 | Erickson .................................. 433/93 |
| 3,924,333 | 12/1975 | Erickson .................................. 433/93 |
| 4,024,642 | 5/1977 | Zorovich .................................. 433/93 |

Primary Examiner—John J. Wilson
Assistant Examiner—Nicholas D. Lucchesi
Attorney, Agent, or Firm—Harness, Dickey & Pierce

[57] ABSTRACT

A dental appliance in the form of a bite block for use during dental surgical operations. Integrally in the bite block is formed at least one aperture serving as an evacuation nozzle for a combined saliva and filling debris aspirator. In one of these apertures is inserted a suction nozzle associated with an aspiration device. This bite block thus is the only extra instrument that the dentist needs to place in the oral cavity of the patient in addition to his working tools.

4 Claims, 2 Drawing Sheets

DENTAL APPLIANCE

BACKGROUND OF THE INVENTION

The subject invention concerns a bite block or mouth prop to be used primarily as an aid in the conduct of dental surgical operations.

One advantage in using a bite block during dental surgical operations is the added comfort to the patient as he may relax his jaw muscles instead of tensioning them to keep his mouth open over prolonged periods.

One example of a prior-art bite block is the "Mouth Prop" sold by McKesson Equipment Co. of Great Britain Ltd. Bite blocks of this kind are used primarily within the health car but only sparingly in dental surgical operations. One reason for their rare use in dental surgical operations probably is that for such operations the dentist must also use pump and suction devices to remove saliva as well as amalgam and other filling debris. Considering that the dentist requires other tools and appliances to perform his work, the use of bite blocks would mean that the dentist's work space inside the patient's oral cavity would be very reduced.

Usually, only a saliva pump is placed in the patient's mouth while an assistant nurse holds and manually operates an aspirator to suck up large pieces of amalgam and other filling debris which come loose during the drilling and filling operations. However, this arrangement leaves much to be desired, since comparatively large amounts of mercury fumes and dust are freed when drilling operations are performed in amalgam fillings. Such fumes are detrimental to the health and should not be allowed to reach the patient's pharynx area. A reduction to an acceptable level of the amount of fumes and dust reaching the patient's pharynx would be possible only if the amalgam aspirator pipe were to remain in the patient's oral cavity during the duration of the dental surgical operation. The aspirator would then create a vacuum pressure inside the patient's oral cavity, preventing the dangerous fumes and dust from reaching the pharynx area and be swallowed by the patient.

No viable solution is available today to the problem of how to allow the amalgam aspirator to be accommodated inside the oral cavity of the patient and remain in that position during the entire dental surgical operation without causing discomfort to the patient or impeding the dentist's work.

Various dental appliances have been suggested to serve as aids in dental surgical operations for removal of filling debris, e.g. in U.S. Pat. Nos. 3,090,122; 3,924,333; 4,192,071; 4,024,642; and 4,281,986. These prior-art appliances are, however, quite bulky and designed in such a manner that they occupy a major portion of the patient's oral cavity. Quite apart from the discomfort to the patient, such bulky contraptions also are apt to initiate the patient's vomiting reflexes. In addition, they reduce the space in which the dentist is able to work and therefore they fail to function as efficient aids in dental surgical operations. More important still, from a technical viewpoint, is that these prior-art appliances are formed with a complicated system of suction channels, resulting in poor suction efficiency and obvious risks for obturation and blockage of the channels.

SUMMARY OF THE INVENTION

The purpose of the subject invention is to provide an improved dental appliance in the form of a bite block for use primarily as an aid in the conduct of dental surgical operations and in which all disadvantages outlined in the aforegoing are removed.

This is achieved in a bite block which is adapted for application between the upper jaw and the lower jaw of the patient and which is characterized therein that the teeth-contacting faces of the bite block form an angle relative to one another corresponding to the angle formed by the open jaws of the patient when the bite block is placed in its operative position and that at least one aperture is formed integrally with the bite block so as to serve as an evacuation nozzle to be connected to a aspiration device.

Further characteristics of the invention will appear from the dependent claims and the following description of a preferred embodiment.

BRIEF DESCRIPTION OF THE DRAWINGS

The invention will be described in closer detail in the following with reference to the accompanying drawings, wherein.

DETAILED DESCRIPTION OF A PREFERRED EMBODIMENT

Figure 1:
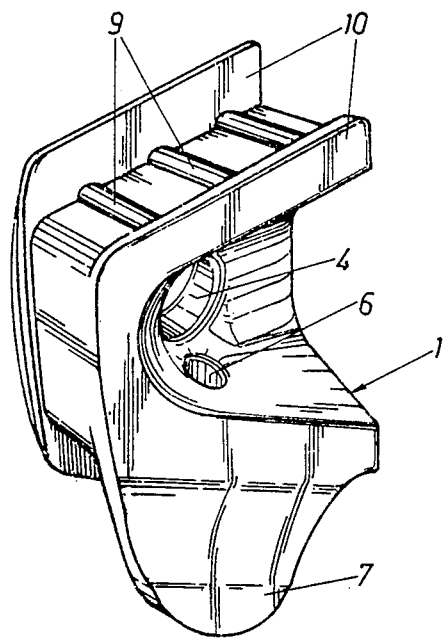
FIGS. 1 and 2 are perspective views showing the bite block in accordance with the invention from two opposite directions.
Figure 2:
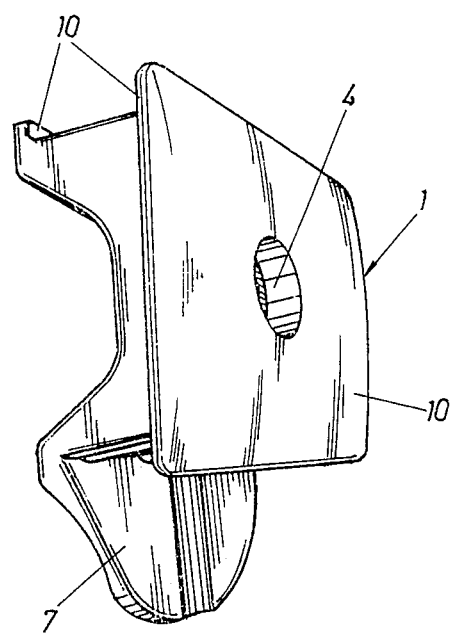
Figure 3:
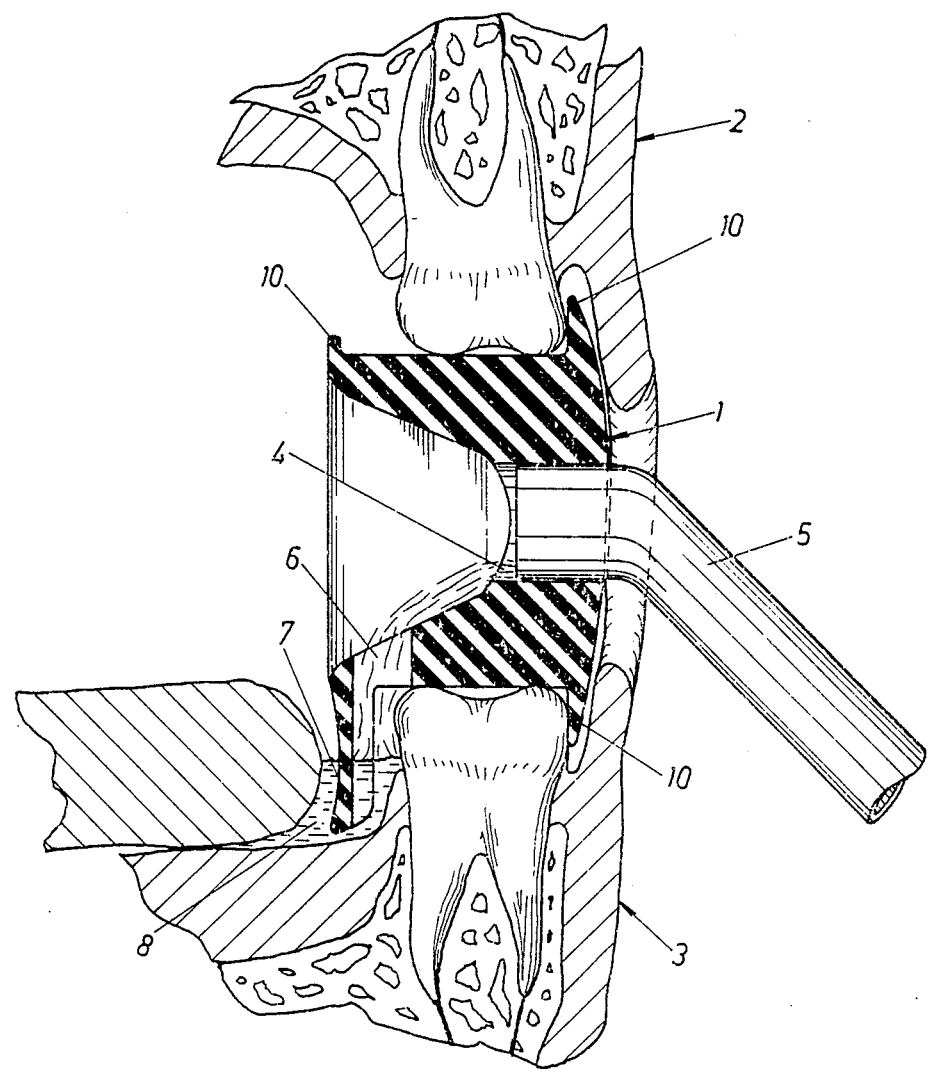
FIG. 3 is a cross section through the bite block in operative position between the upper and lower jaws of the patient.

The bite block 1 in accordance with the invention is intended to be positioned in the manner known per se between the upper jaw 2 and the lower jaw 3 of the patient in order to maintain the patient's mouth in an open position, allowing easy access for dental surgical operations and optimum working conditions while providing maximum comfort to the patient.

The bite block 1 is provided with one through-aperture 4 designed to receive the suction nozzle of an aspiration device, not shown. The bite block presents a second, vertically extending aperture 6 adjacent and in communication with the through-aperture 4, said second aperture 6 forming a saliva aspiration means together with a depending lip 7 which in the operative position of the appliance abuts against the inner face of the patient's lower jaw. Upon activation of the aspiration device with which the suction nozzle is connected, the air flowing past the vertical aperture 6 generates a vacuum pressure inside the aperture 6, resulting in saliva 8 being sucked up through the vertical aperture 6 and conducted to the aspiration device via the aperture 4 and the nozzle 5 attached thereto.

In order to ensure that the bite block remains in the operative position inside the patient's mouth the faces of contact of the bite block against the patient's teeth present a number of transverse ribs 9. For the same purpose, upstanding rims 10 border the abutment faces of the bite block 1 so as to prevent the latter from being displaced laterally.

On account of its asymmetrical configuration, the bite block in accordance with the invention is manufactured in a left-jaw as well as a right-jaw version.

The advantage of the bite block in accordance with the invention is that the dentist needs place only one single appliance in the mouth, of the patient in order to conduct the dental surgical operations, using the bite block 1. In addition to serving as a means of maintaining the patient's mouth open in a relaxed position, the bite block 1 also replaces the conventional pump and suction devices, i.e. the conventional saliva pump as well as the debris aspiration pipe.

Finally, it should be mentioned that the invention is not limited to the embodiment as described in the aforegoing and illustrated in the drawings but that a number of alternative embodiments ar possible within the scope of the appended claims.

What I claim is:

1. A bite block to be used primarily during dental surgical operations and adapted to assume an operative position between the upper jaw and the lower jaw of a patient, said bite block comprising:
   an upper bite face adapted to engage teeth on the upper jaw of the patient and a lower bite face adapted to engage teeth on the lower jaw of the patient when the bite block is in the operative position, said lower bite face substantially wider than the teeth on the lower jaw;
   a recess in an interior surface of said bite block between said upper and lower bite faces, said recess substantially open in a longitudinally forward direction;
   a first aperture extending in a transverse direction from an exterior surface of said bite block through said bite block to said recess, said first aperture defining a port in said exterior surface adapted to receive an evacuation nozzle of an aspiration device and said first aperture providing fluid communication between said recess and said port;
   an interior rim extending in a substantially vertical direction below said lower bite face, said interior rim defining a saliva reservoir bounded by said interior rim, said lower bite face, and the teeth of the lower jaw when said bite block is in the operative position; and
   a second aperture extending substantially in a vertical direction from said saliva reservoir through said lower bite face to said recess, said second aperture providing fluid communication between said saliva reservoir and said recess.

2. A bite block as claimed in claim 1, comprising transversely extending ribs formed on the upper and lower faces of said bite block, said ribs in contact with the patient's teeth when bite block is in the operative position.

3. A bite block as claimed in claim 1, further comprising interior and exterior rims of said upper bite face upwardly projecting beyond said upper bite face and formed along both marginal edges of said upper bite face.

4. A bite block as claimed in claim 1, further comprising an exterior rim of said lower bite face extending in a substantially vertical direction below said lower bite face and substantially in contact with the teeth of the lower jaw when said bite block is in the operative position.

* * * * *